(12) United States Patent
Stulen et al.

(10) Patent No.: US 9,907,600 B2
(45) Date of Patent: Mar. 6, 2018

(54) ULTRASONIC ANASTOMOSIS INSTRUMENT WITH PIEZOELECTRIC SEALING HEAD

(71) Applicant: Ethicon Endo-Surgery, Inc., Cincinnati, OH (US)

(72) Inventors: Foster B. Stulen, Mason, OH (US); Timothy G. Dietz, Wayne, PA (US)

(73) Assignee: Ethicon LLC, Guaynabo, PR (US)

( * ) Notice: Subject to any disclaimer, the term of this patent is extended or adjusted under 35 U.S.C. 154(b) by 555 days.

(21) Appl. No.: 14/081,190

(22) Filed: Nov. 15, 2013

(65) Prior Publication Data

US 2015/0141976 A1  May 21, 2015

(51) Int. Cl.
| | | |
|---|---|---|
| *A61B 18/18* | (2006.01) | |
| *A61B 18/04* | (2006.01) | |
| *A61N 7/00* | (2006.01) | |
| *A61B 17/11* | (2006.01) | |
| A61B 17/00 | (2006.01) | |
| A61B 18/00 | (2006.01) | |
| A61B 17/115 | (2006.01) | |

(52) U.S. Cl.
CPC .............. *A61B 18/04* (2013.01); *A61B 17/11* (2013.01); *A61N 7/00* (2013.01); *A61B 17/1155* (2013.01); *A61B 2017/00504* (2013.01); *A61B 2017/00513* (2013.01); *A61B 2018/00184* (2013.01); *A61B 2018/00619* (2013.01); *A61N 2007/0043* (2013.01)

(58) Field of Classification Search
CPC .......... A61B 18/04; A61B 2018/00607; A61B 2018/0063

USPC .............................................. 606/27, 28, 169
See application file for complete search history.

(56) References Cited

U.S. PATENT DOCUMENTS

| | | |
|---|---|---|
| 5,205,459 A | 4/1993 | Brinkerhoff et al. |
| 5,271,544 A | 12/1993 | Fox et al. |
| 5,275,322 A | 1/1994 | Brinkerhoff et al. |

(Continued)

FOREIGN PATENT DOCUMENTS

| | | |
|---|---|---|
| EP | 0 695 535 A1 | 2/1996 |
| WO | WO 2011/047857 A1 | 4/2011 |

OTHER PUBLICATIONS

U.S. Appl. No. 13/657,553, filed Oct. 22, 2012.

(Continued)

*Primary Examiner* — Michael Peffley
*Assistant Examiner* — Amanda Zink
(74) *Attorney, Agent, or Firm* — Frost Brown Todd LLC

(57) ABSTRACT

An apparatus includes a body, a shaft, an ultrasonic element, and an annular clamp pad. The shaft extends distally from the body. The ultrasonic element is located at the distal end of the shaft. The ultrasonic element includes a distally presented annular face. The clamp pad is movable toward the distally presented annular face of the ultrasonic element. When tissue is compressed between the clamp pad and the distally presented annular face of the ultrasonic element, the ultrasonic element may be activated with ultrasonic energy. The resulting ultrasonic vibrations may sever and seal the tissue captured between the distally presented annular face and the clamp pad, resulting in an anastomosis. The apparatus may thus be used to join two hollow tubular tissue structures, such as portions of a gastrointestinal tract.

17 Claims, 11 Drawing Sheets

(56) References Cited

U.S. PATENT DOCUMENTS

| | | | |
|---|---|---|---|
| 5,285,945 A | 2/1994 | Brinkerhoff et al. | |
| 5,292,053 A | 3/1994 | Bilotti et al. | |
| 5,322,055 A | 6/1994 | Davison et al. | |
| 5,333,773 A | 8/1994 | Main et al. | |
| 5,350,104 A * | 9/1994 | Main | A61B 17/115 227/179.1 |
| 5,395,030 A | 3/1995 | Kuramoto et al. | |
| 5,471,988 A * | 12/1995 | Fujio | A61B 8/12 600/439 |
| 5,533,661 A | 7/1996 | Main et al. | |
| 5,873,873 A | 2/1999 | Smith et al. | |
| 5,980,510 A | 11/1999 | Tsonton et al. | |
| 6,004,335 A * | 12/1999 | Vaitekunas | A61B 17/07207 227/180.1 |
| 6,325,811 B1 | 12/2001 | Messerly | |
| 6,773,444 B2 | 8/2004 | Messerly | |
| 6,783,524 B2 | 8/2004 | Anderson et al. | |
| 7,935,114 B2 | 5/2011 | Takashino et al. | |
| 8,461,744 B2 | 6/2013 | Wiener et al. | |
| 8,562,547 B2 * | 10/2013 | Babaev | A61B 17/320068 601/2 |
| 8,591,536 B2 | 11/2013 | Robertson | |
| 8,623,027 B2 | 1/2014 | Price et al. | |
| 9,005,144 B2 | 4/2015 | Slayton et al. | |
| 9,198,635 B2 | 12/2015 | Crum et al. | |
| 2002/0111620 A1 * | 8/2002 | Cooper | A61B 8/445 606/41 |
| 2003/0013960 A1 * | 1/2003 | Makin | A61B 8/12 600/439 |
| 2003/0018270 A1 * | 1/2003 | Makin | A61B 8/12 600/466 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0183109 A1 * | 7/2008 | Babaev | A61B 17/320068 601/2 |
| 2008/0200940 A1 | 8/2008 | Eichmann et al. | |
| 2010/0069940 A1 | 3/2010 | Miller et al. | |
| 2011/0087212 A1 | 4/2011 | Aldridge et al. | |
| 2012/0112687 A1 | 5/2012 | Houser et al. | |
| 2012/0116265 A1 | 5/2012 | Houser et al. | |
| 2012/0292372 A1 | 11/2012 | Nalagatla et al. | |
| 2013/0197550 A1 | 8/2013 | Dietz et al. | |
| 2014/0005701 A1 | 1/2014 | Olson et al. | |

OTHER PUBLICATIONS

U.S. Appl. No. 13/716,323, filed Dec. 17, 2012.
U.S. Appl. No. 14/032,842, filed Sep. 20, 2013.
U.S. Appl. No. 14/033,688, filed Sep. 23, 2013.
U.S. Appl. No. 14/033,751, filed Sep. 23, 2013.
U.S. Appl. No. 61/410,603, filed Nov. 5, 2010.
International Search Report and Written Opinion dated Jan. 29, 2015 for Application No. PCT/US2014/064996, 13 pgs.

* cited by examiner

ULTRASONIC ANASTOMOSIS INSTRUMENT WITH PIEZOELECTRIC SEALING HEAD

BACKGROUND

An anastomosis may be formed in a patient to join two hollow tissue structures together and thereby provide fluid communication between those two hollow tissue structures. The anastomosis may have a sealed outer perimeter that prevents unwanted leakage from the anastomosis site. The anastomosis may include a side-to-side anastomosis (e.g., joining a sidewall of an intestine to the sidewall of the stomach, etc.) or an end-to-end anastomosis (e.g., joining the free ends of two tubular tissue structures together). For instance, in some surgical procedures, portions of the gastrointestinal tract may be cut and removed to eliminate undesirable tissue or for other reasons. Once the undesirable tissue is removed, the remaining portions of the gastrointestinal tract may be recoupled together in an anastomisis. One instrument that may be used to accomplish these anastomotic procedures is a circular stapler that is inserted through a naturally occurring orifice in a patient and/or through a surgically created orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; U.S. Pat. No. 5,533,661, entitled "Surgical Anastomosis Stapling Instrument," issued Jul. 9, 1996; U.S. Pub. No. 2012/0292372, entitled "Low Cost Anvil Assembly for a Circular Stapler," published Nov. 22, 2012, now U.S. Pat. No. 8,910,847, issued Dec. 16, 2014; and U.S. patent application Ser. No. 14/033,688, entitled "Surgical Stapler with Rotary Cam Drive and Return," filed Sep. 23, 2013, published as U.S Pub. No. 2015/0083772 on Mar. 26, 2015, the disclosure of which is incorporated by reference herein. The disclosure of each of the above-cited U.S. Patents and U.S. Patent Application Publication is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of tubular tissue structures.

In lieu of having staple driving features, a variety of surgical instruments include an end effector having a blade element that vibrates at ultrasonic frequencies to cut and seal tissue (e.g., by denaturing proteins in tissue cells) or to just seal tissue. These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein; and U.S. patent application Ser. No. 13/745,385, entitled "Ultrasonic Surgical Apparatus with Silicon Waveguide," filed Jan. 18, 2013, published as U.S. Pat. Pub. No. 2013/0197550 on Aug. 1, 2013, now U.S. Pat. No. 9,737,735, issued Aug. 22, 2017, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," now expired, the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," published as U.S. Pat. Pub. No. 2014/0005701 on Jan. 2, 2014, now U.S. Pat. No. 9,393,037, issued Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," published as U.S. Pat. Pub. No. 2014/0114334 on Apr. 24, 2014, now U.S. Pat. No. 9,095,367 issued on Aug. 4, 2014, the disclosure of which is incorporated by reference herein.

While various kinds of instruments and techniques have been made and used to join hollow anatomical structures at an anastomosis site, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
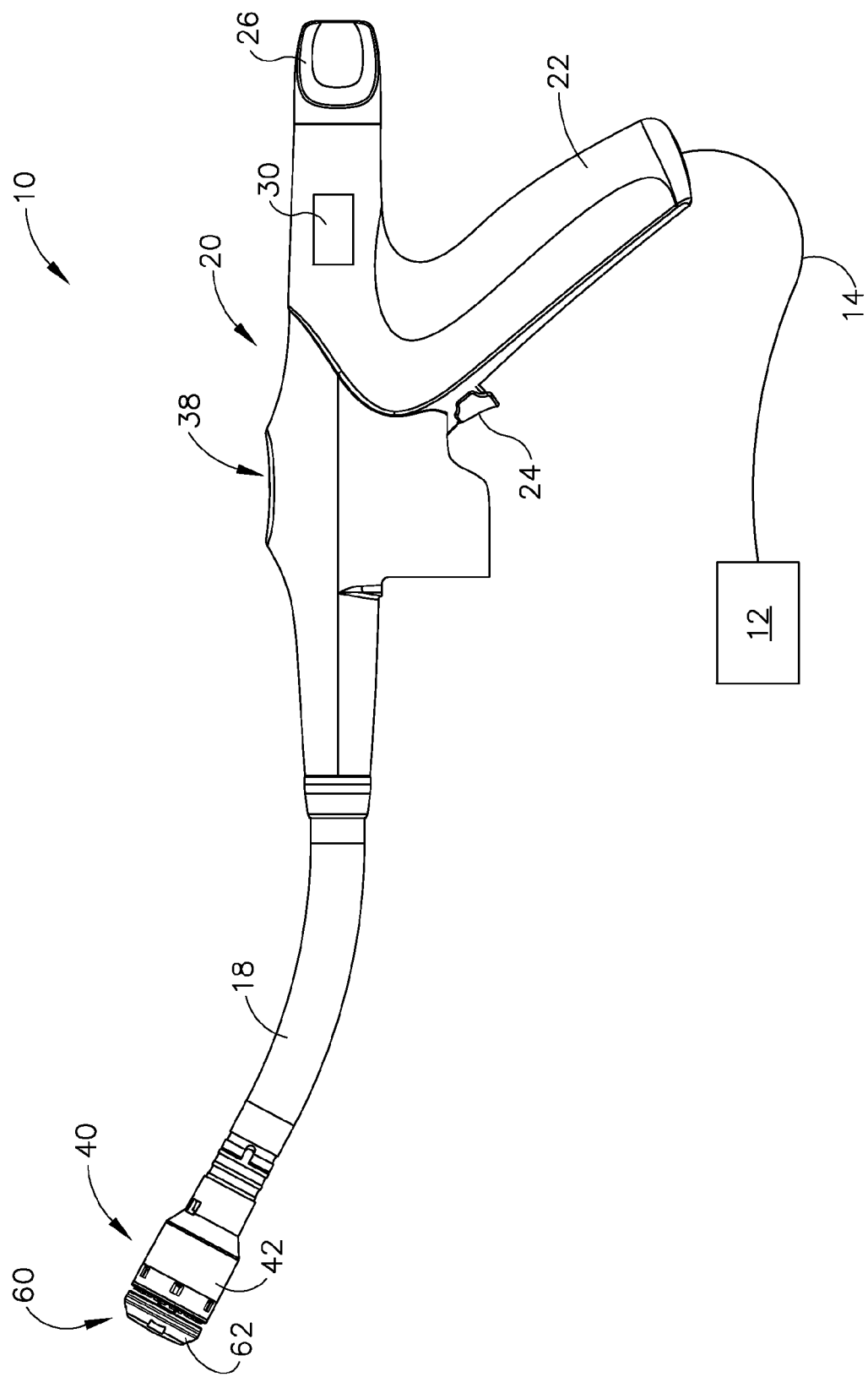
FIG. 1 depicts a side elevational view of an exemplary ultrasonic anastomosis instrument, with an anvil coupled with the ultrasonic head assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Anastomosis Instrument

Figure 2:
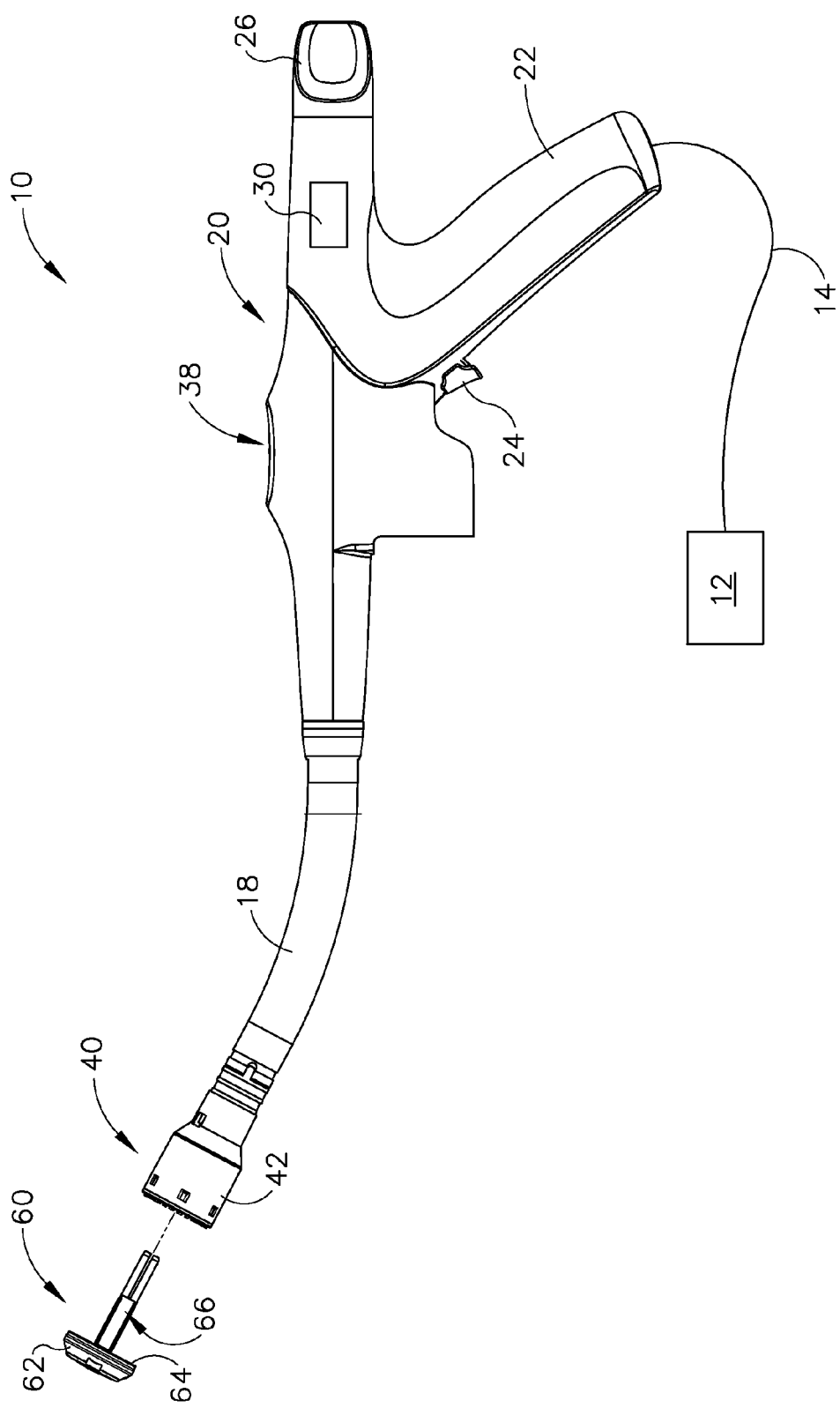
FIG. 2 depicts a side elevational view of the instrument of FIG. 1, with the anvil decoupled from the ultrasonic head assembly.

FIGS. 1-2 depict an exemplary anastomosis instrument (10) having a handle assembly (20), an ultrasonic head assembly (40), a shaft assembly (18), and an anvil (60), each of which will be described in greater detail below. Shaft assembly (18) extends distally from handle assembly (20). Ultrasonic head assembly (40) is located at the distal end of shaft assembly (18). Anvil (60) is configured to removably couple with a trocar (34) of shaft assembly (18) and thereby compress tissue against ultrasonic head assembly (40). Handle assembly (20) is then operable to actuate a transducer element (70) of ultrasonic head assembly (40) to transect and seal tissue that is captured between ultrasonic head assembly (40) and anvil (60). Accordingly, anastomosis instrument (10) may be used to join the free ends of two tubular tissue structures (100, 110) together in a sealed fashion at an anastomosis (140) site, as shown in FIG. 6A-6F. Exemplary features of instrument (10) will be described in greater detail below, while numerous variations will be apparent to those of ordinary skill in the art in view of the teachings herein.

In addition to the teachings below, it should be understood that one or more of the ultrasonic features of instrument (10) may be constructed in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750, now U.S. Pat. No. 8,623,027; U.S. Pub. No. 2010/0069940, now U.S. Pat. No. 9,203,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265; U.S. patent application Ser. No. 13/538,588, now U.S. Pat. No. 9,393,037; U.S. patent application Ser. No. 13/657,553, now U.S. Pat. No. 9,095,367; and/or U.S. Pat. App. No. 61/410,603. The disclosures of each of the foregoing patents, publications, and applications are incorporated by reference herein.

A. Exemplary Handle Assembly

Handle assembly (20) of the present example includes a pistol grip (22), a trigger assembly (24), a knob (26), and a trocar actuation assembly (30). It should be understood that pistol grip (22) is merely optional, such that handle assembly (20) may provide any other suitable kind of gripping feature(s). A cable (16) extends from pistol grip (22) and is further coupled with a generator (12). Generator (12) is operable to selectively provide power to transducer element (70) of ultrasonic head assembly (40). By way of example only, generator (12) may comprise a GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (12) may be integrated into handle assembly (20), and that handle assembly (20) may even include a battery or other on-board power source such that cable (14) is omitted. Still other suitable forms that generator (12) may take, as well as various features and operabilities that generator (12) may provide, will be apparent to those of ordinary skill in the art in view of the teachings herein.

Trigger assembly (24) is pivotable toward pistol grip (22) to selectively couple generator (12) with transducer element (70) of ultrasonic head assembly (40), to thereby selectively activate transducer element (70). In some versions, trigger assembly (24) includes a safety feature that prevents inadvertent actuation of trigger assembly (24). In some such versions, the safety feature effectively disables trigger assembly (24) or otherwise prevents actuation of trigger assembly (24) when anvil (60) is outside of a predetermined range of distance from ultrasonic head assembly (40). Once anvil (60) reaches a position where it is within the predetermined range of distance from ultrasonic head assembly (40), the safety feature may enable actuation of trigger assembly (24). By way of example only, such a safety feature may be constructed in accordance with at least some of the teachings of U.S. patent application Ser. No. 14/033,751, entitled "Control Features for Motorized Surgical Stapling Instrument," filed Sep. 24, 2013, published as U.S. Pub. No. 2015/0083774 on Mar. 26, 2015, the disclosure of which is incorporated by reference herein. Other suitable ways in which a safety feature of trigger assembly (24) may be configured will be apparent to those of ordinary skill in the art in view of the teachings herein. Similarly, other suitable features and configurations for trigger assembly (24) will be apparent to those of ordinary skill in the art in view of the teachings herein.

Knob (26) is rotatable to selectively actuate trocar actuation assembly (30). As will be described in greater detail below, trocar actuation assembly (30) is operable to selectively translate a trocar (34), to thereby selectively adjust the position of anvil (60) relative to ultrasonic head assembly (40). In particular, rotation of knob (26) in one direction causes anvil (60) to retract proximally toward ultrasonic head assembly (400); while rotation of knob (26) in the other direction causes anvil (60) to advance distally toward ultrasonic head assembly (400). Trocar actuation assembly (30) is thus operable to convert rotary motion of knob (26) into linear motion of trocar (34) and anvil (60). By way of example only, trocar actuation assembly (30) may be constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; U.S. Pub. No. 2012/0292372, now U.S. Pat. No. 8,910,847; and/or U.S. patent application Ser. No. 14/033,688, published as U.S. Pub. No. 2015/0083772, the disclosures of all of which are incorporated by reference herein. Other suitable ways in which trocar actuation assembly (30) may be configured will be apparent to those of ordinary skill in the art in view of the teachings herein.

B. Exemplary Shaft Assembly

In the present example shaft assembly (18) has a rigidly curved configuration, which may facilitate positioning of ultrasonic head assembly (40) in a patient's colon from a rectal approach. In some other versions, shaft assembly (18) is rigidly straight. In still other versions, shaft assembly (18) is flexible. As yet another merely illustrative alternative, shaft assembly (18) may be operable to selectively transition between a flexible configuration and a rigid configuration. By way of example only, such selective transitioning may be provided in accordance with at least some of the teachings of U.S. patent application Ser. No. 13/716,323, entitled "Motor Driven Rotary Input Circular Stapler with Lockable Flexible Shaft," filed Dec. 17, 2012, now U.S. Pat. No. 9,463,022, issued Oct. 11, 2016, the disclosure of which is incorporated by reference herein.

Figure 4:
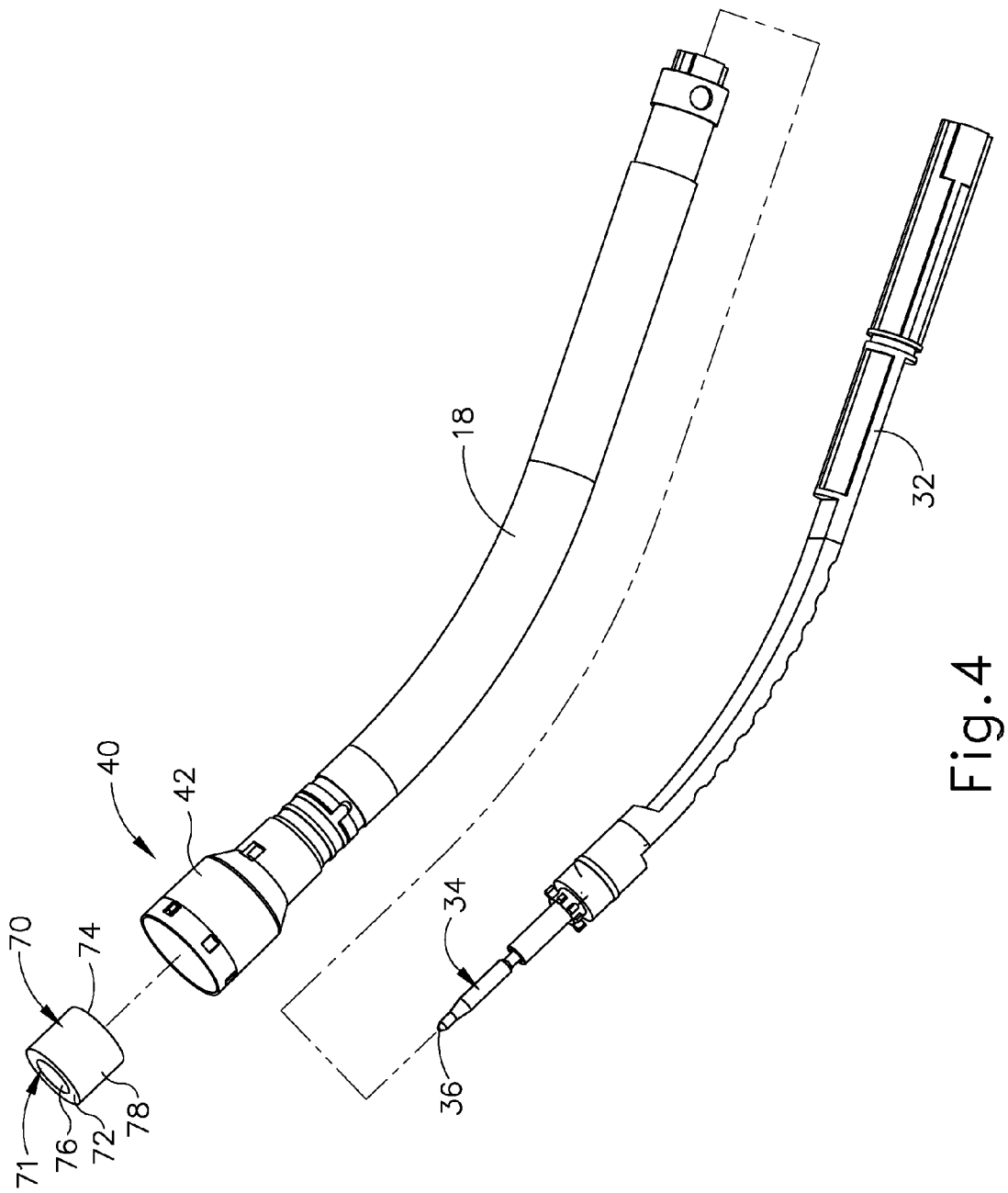
FIG. 4 depicts an exploded view of the shaft assembly and ultrasonic head assembly of the instrument of FIG. 1.

As best seen in FIG. 4, shaft assembly (18) of the present example includes a trocar actuation shaft (32), which is operable to translate within shaft assembly (18). Trocar (34) is secured to the distal end of trocar actuation shaft (32), such that trocar (34) translates unitarily with trocar actuation shaft (32). Trocar actuation shaft (32) is coupled with trocar actuation assembly (30), such that trocar actuation assembly (30) is operable to translate trocar (34) via trocar actuation shaft (32). Various suitable ways in which trocar actuation shaft (32) may be coupled with trocar actuation assembly (30) will be apparent to those of ordinary skill in the art in view of the teachings herein.

Trocar (34) is configured for selective insertion into a shank (66) of anvil (60), which will be described in greater detail below. Trocar (34) of the present example includes a tapered distal tip (36). Such a tip (34) may be capable of piercing through tissue and/or aiding the positioning of shank (66) of anvil (60) onto trocar (34), though the tapered configuration of tip (36) is merely optional. For instance, in other versions trocar (34) may have a blunt tip (36). In addition, or in the alternative, trocar (34) may include a magnetic portion (not shown) that may attract anvil (60) toward trocar (34). Still further configurations and arrangements for trocar (34) will be apparent to those of ordinary skill in the art in view of the teachings herein.

C. Exemplary Ultrasonic Head Assembly

Figure 5:
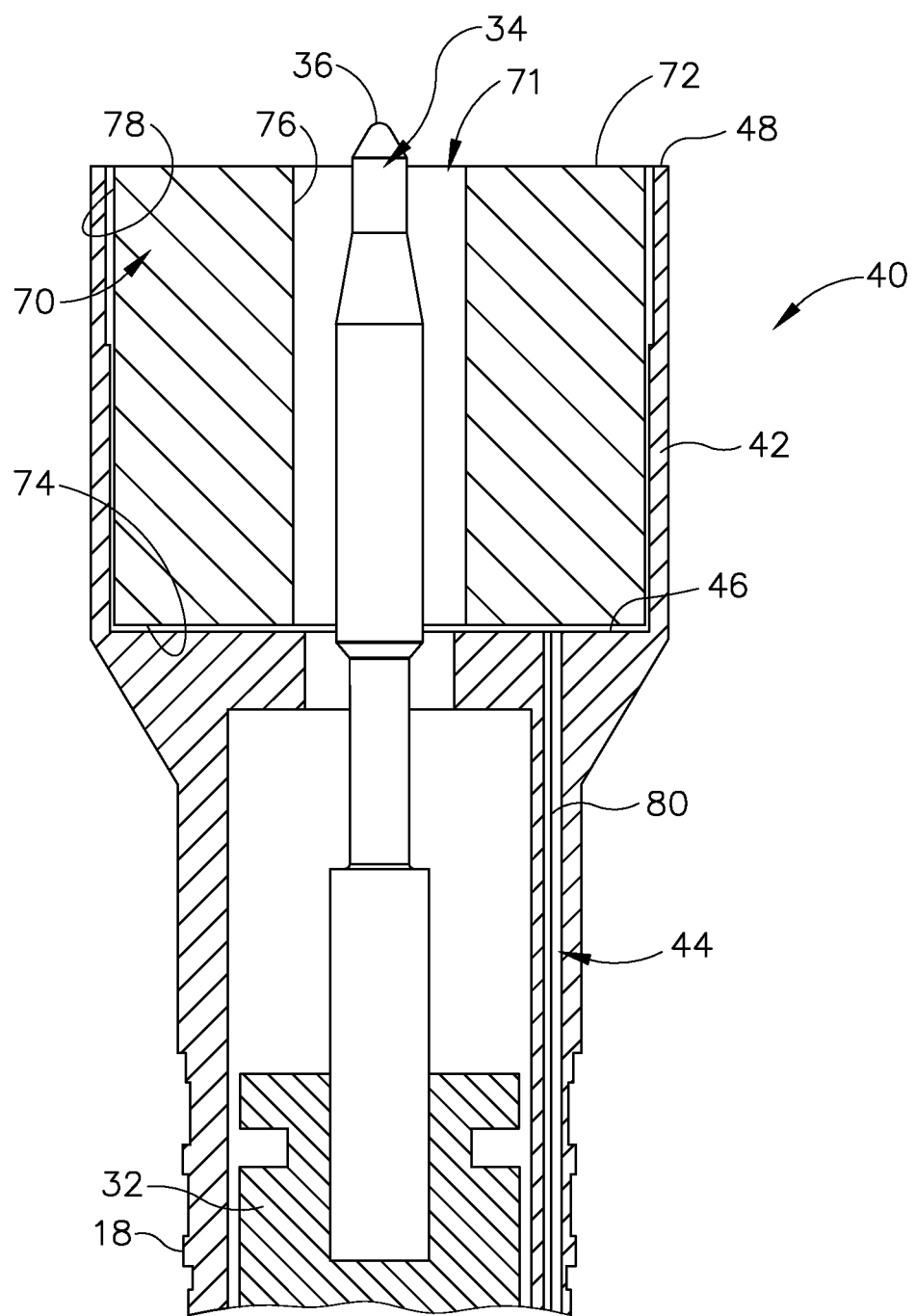
FIG. 5 depicts a side cross-sectional view of the ultrasonic head assembly of the instrument of FIG. 1.

Ultrasonic head assembly (40) of the present example comprises a shroud (42) defining a socket that is sized to receive transducer element (70). By way of example only, shroud (42) may comprise aluminum and/or any other suitable material(s). Transducer element (70) is formed of a piezoelectric material such that transducer element (70) is configured to convert electrical power from generator (12) into ultrasonic vibrations. As best seen in FIGS. 4-5, transducer element (70) of the present example consists of a single, monolithic piece of piezoelectric material that defines a bore (71), such that transducer element (70) has a hollow, elongate, cylindraceous configuration. Transducer element (70) thus includes a distal face (72), a proximal face (74), an inner diameter surface (76), and an outer diameter surface (78). As one merely illustrative alternative, transducer element (70) may be formed by a plurality of piezoelectric disc elements coaxially arranged in a stack. Other suitable forms that transducer element (70) may take will be apparent to those of ordinary skill in the art in view of the teachings herein.

In some versions, transducer element (70) is received in shroud (42) through an interference fit, such that shroud (42) applies radially inwardly directed compressive forces on outer diameter surface (78). In some versions, an acoustic insulator is interposed between transducer element (70) and opposing surfaces of shroud (40). As yet another merely illustrative example, shroud (42) may include an inwardly directed annular protrusion that applies inwardly directed compression on transducer element (70) at a longitudinal position that corresponds to a node associated with resonant ultrasonic vibrations communicated through transducer element (70). It should also be understood that one or more features may be positioned over distal face (72). For instance, a metallic washer may be positioned over distal face (72) to provide protection while also providing acoustic transmissivity. By way of example only, such a washer may comprise titanium (Ti6Al4V) and/or any other suitable material(s). Trocar (34) is coaxially positioned within bore (71). As shown in FIGS. 5-6B, the diameter of bore (71) is large enough to allow trocar (34) to freely translate distally and proximally relative to transducer element (70). As shown in FIGS. 6C-6E, bore (71) is also sized to accommodate a shank (66) of anvil (60), such that shank (66) may enter bore (71) without contacting inner diameter surface (76).

Faces (72, 74) are electrically insulated (e.g., by a coating, film, other feature, etc.); while surfaces (76, 78) are electrically conductive (e.g., with a metallic plating, etc.). Transducer element (70) is configured to convert electrical power into ultrasonic vibrations when a voltage is applied to surfaces (76, 78) (e.g., with surface (76) serving as a ground or neutral path). By way of example only, transducer element (70) may be configured in accordance with at least some of the teachings of U.S. patent application Ser. No. 13/745,385, entitled "Ultrasonic Surgical Apparatus with Silicon Waveguide," filed Jan. 18, 2013, now U.S. Pat. No. 9,737,735, issued Aug. 22, 2017, the disclosure of which is incorporated by reference herein.

Electrical power from generator (12) reaches transducer element (70) via wires (80), which are disposed in a passageway (44) formed through ultrasonic head assembly (40) and shaft assembly (18). Wires (80) are in selective electrical communication with cable (14) and thus generator (12), based on actuation of trigger assembly (24). Wires (80) may be coupled with transducer element (70) in various ways. By way of example only, wires (80) may be coupled with transducer element (70) in accordance with at least some of the teachings of U.S. patent application Ser. No. 14/032,842, entitled "Transducer Features for Ultrasonic Surgical Instrument," filed Sep. 20, 2013, published as U.S. Pub. No. 2015/0088178 on Mar. 26, 2015, the disclosure of which is incorporated by reference herein. It should be understood that wires (80) are merely illustrative, and that any other suitable kind of electrical conductor(s) may be used. Other suitable ways in which transducer element (70) may receive electrical power will be apparent to those of ordinary skill in the art in view of the teachings herein.

In the present example, distal face (72) of transducer element (70) is located at a position corresponding to an anti-node associated with resonant ultrasonic vibrations communicated through transducer element (70). When transducer element (70) is energized, distal face (72) is configured to move axially/longitudinally and/or radially in the range of, for example, approximately 10 to 500 microns peak-to-peak, and in some instances in the range of about 20 to about 200 microns at a predetermined vibratory resonant frequency $f_o$ of, for example, 55.5 kHz. When transducer element (70) of the present example is activated, distal face (72) thus vibrates axially/longitudinally and/or radially at the resonant ultrasonic frequency. Accordingly, when tissue is clamped between distal face (72) of transducer element (70) and a clamp pad (64) of anvil (60) as will be described in greater detail below, the ultrasonic oscillation of transducer element (70) in the axial/longitudinal direction and/or in the radial direction may simultaneously sever the tissue and denature the proteins in adjacent tissue cells, thereby providing a coagulative effect with relatively little thermal spread. In some versions, an electrical current may also be provided through transducer element (70) and/or clamp pad (64) to also cauterize the tissue.

In the present example, distal face (72) of transducer element (70) is flush with the distal edge (48) of shroud (42). In some other versions, distal face (72) of transducer element (70) protrudes distally past distal edge (48) of shroud (42). In still other versions, distal face (72) of transducer element (70) is proximally recessed relative to distal edge (48) of shroud (42). In versions where distal face (72) of transducer element (70) is proximally recessed relative to distal edge (48) of shroud (42), clamp pad (64) may be configured to protrude proximally past distal edge (48) of shroud (42) when anvil (60) is in a fully retracted position relative to ultrasonic head assembly (40). Other suitable relationships between these structural features will be apparent to those of ordinary skill in the art in view of the teachings herein.

It should be understood that transducer element (70) may be varied in numerous ways. By way of example only, transducer element (70) may comprise a stack of coaxially arranged piezoelectric ring structures, similar to piezoelectric arrangements as taught in various references that are cited herein. It should also be understood that an endmass may be longitudinally interposed between proximal face (74) of transducer element (70) and a distally facing surface (46) within shroud (42) of ultrasonic head assembly (40). Such an endmass may be in the form of a disk and/or any other suitable kind of structure. In some other versions, a transducer assembly is positioned in handle assembly (20)

(e.g., within pistol grip (22), etc.), and an acoustic waveguide extends through shaft assembly (18) to reach a cylindraceous blade that is located in ultrasonic head assembly (40), such that ultrasonic vibrations generated by the transducer assembly are communicated to the cylindraceous blade. Such a cylindraceous blade may have a configuration that is substantially similar to the configuration of transducer element (70), such that the cylindraceous blade cooperates with anvil (60) just like transducer element (70). In such versions where shaft assembly (18) has a bent configuration or the waveguide otherwise needs to bend along a curved path, the waveguide may be constructed in accordance with at least some of the teachings of U.S. patent application Ser. No. 13/538,588, now U.S. Pat. No. 9,393,037, and/or U.S. patent application Ser. No. 13/657,553, now U.S. Pat. No. 9,095,367, the disclosures of which are incorporated by reference herein. Other suitable variations will be apparent to those of ordinary skill in the art in view of the teachings herein.

D. Exemplary Anvil

Figure 3:
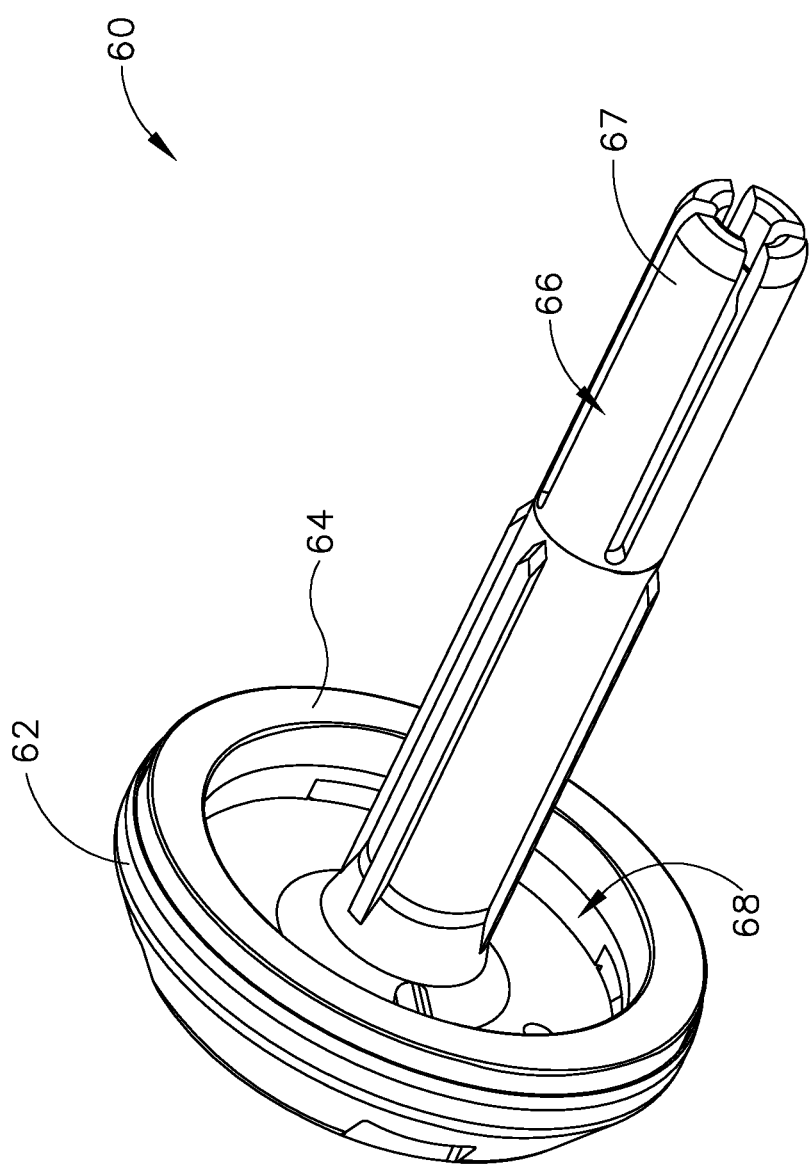
FIG. 3 depicts a perspective view of the anvil of the instrument of FIG. 1.

As best seen in FIG. 3, anvil (60) of the present example comprises a head (62) and a shank (66). Head (62) includes a proximally facing annular clamp pad (64). In some versions, clamp pad (64) comprises polytetrafluoroethylene (PTFE). For instance, clamp pad (64) may comprise steel coated with PTFE or some other low-friction material. As another merely illustrative example, clamp pad (64) may comprise a combination of polyimide, graphite, and PTFE. Other suitable materials (and combinations thereof) that may be used to form clamp pad (64) will be apparent to those of ordinary skill in the art in view of the teachings herein. It should also be understood that clamp pad (64) may be substantially flat or may include various kinds of surface features. For instance, clamp pad (64) may include knurling, an angularly spaced array of radially extending ridges (e.g., in a starburst pattern, etc.), an array of concentric annular ridges, criss-crossing ridges, and/or various other kinds of surface features. Clamp pad (64) may also be tapered. For instance, the exposed surface of clamp pad (64) may be tapered such that the clamp pad (64) has a thickness at the inner diameter of clamp pad (64) that is greater than the thickness at the outer diameter of clamp pad (64). As another merely illustrative example, clamp pad (64) may be tapered such that clamp pad (64) has a cross-sectional profile of an equilateral triangle with rounded corners, with a peak oriented toward distal face (72) of transducer element (70) when anvil (60) is coupled with trocar (34).

Clamp pad (64) may also be constructed in accordance with one or more teachings of U.S. Pub. No. 2006/0079874, the disclosure of which is incorporated by reference herein. Clamp pad (64) and/or some other portion of anvil (60) may also include biologics, medical agents, and/or other substances to increase hemostasis and/or healing of tissue. Various suitable biologics, medical agents, and/or other substances to increase hemostasis and/or healing of tissue will be apparent to those of ordinary skill in the art in view of the teachings herein. Similarly, other suitable features and configurations for clamp pad (64) will be apparent to those of ordinary skill in the art in view of the teachings herein.

Head (62) also includes a recess (68) defined between shank (66) and clamp pad (64). Recess (68) is configured to accommodate excess tissue as will be described in greater detail below. As best seen in FIGS. 6A-6E, shank (66) defines a bore (69) that is sized to receive trocar (34). Shank (66) also includes a plurality of leaves (67) that extend to the free end of shank (66). Leaves (67) are resiliently biased to define a cylindraceous configuration; yet are deformable outwardly to enable insertion of trocar (34). Once trocar (34) is inserted into bore (69) of shank (66) to a certain depth, leaves (67) snap inwardly to capture trocar (34), thereby providing a snap fit between shank (66) and trocar (34). In some other versions, shank (66) includes resiliently biased retaining clips that selectively secure shank (66) to trocar (34). In still other versions, shank (66) and/or trocar (34) may include barbs, one-way snaps, collets, collars, tabs, bands, and/or any other suitable features that provide removable or one-way coupling between anvil (60) and trocar (34). By way of further illustration, anvil (60) may couple with trocar (34) in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; U.S. Pub. No. 2012/0292372, now U.S. Pat. No. 8,910,847; and/or U.S. patent application Ser. No. 14/033,688, published as U.S. Pub. No. 2015/0083772, the disclosures of all of which are incorporated by reference herein. As yet another merely illustrative example, anvil (60) may couple with trocar (34) via a threaded stud. It should also be understood that trocar (34) may include a feature similar to bore (69) while shank (66) includes a closed tip similar to tip (36). Still other suitable ways in which anvil (60) may couple with trocar (34) will be apparent to those of ordinary skill in the art in view of the teachings herein.

When anvil (60) is coupled with trocar (34), the distance between the proximally facing surface of clamp pad (64) and distal face (72) of transducer element (70) defines a gap distance d. As noted above, knob (26) may be used to actuate trocar actuation assembly (30), which will adjust the gap distance d based on the direction in which knob (26) is rotated. Once the gap distance d is brought within a predetermined range, trigger assembly (24) may be actuated to activate transducer element (70), to thereby transect and seal tissue captured between clamp pad (64) and distal face (72) of transducer element (70). In order to provide the operator with visual feedback relating to the gap distance d, handle assembly (20) of the present example includes an indicator window (38) with a feature that is operable to provide the user with visual indication of whether the gap distance d is within the predetermined range. By way of example only, indicator window (38) may include a bar that moves in relation to fixed indicia (e.g., in accordance with the teachings of U.S. Pat. No. 5,533,661, the disclosure of which is incorporated by reference herein). Alternatively, indicator window (38) may include one or more LEDs, an LCD screen, and/or any other suitable feature(s) that provide the operator with visual indication of whether the gap distance d is within the predetermined range. In addition or in the alternative, handle assembly (20) may include one or more features that provide an audible indication of whether the gap distance d is within the predetermined range. For instance, an audible feedback feature may provide a particular tone, pattern of tones, or some other audible indication when the gap distance d is within the predetermined range. Still other suitable ways in which instrument (10) may indicate to the operator that the gap distance d is within the predetermined range will be apparent to those of ordinary skill in the art in view of the teachings herein.

It should be understood that proper ultrasonic cutting and sealing of tissue interposed between distal face (72) of transducer element (70) and clamp pad (64) of anvil (60) may depend on the amount of pressure or compression force being exerted on the tissue by distal face (72) and clamp pad (64). It should be understood that the gap distance d may correlate with a preferred compression force. Alternatively, actuation of trocar actuation shaft (32) may be focused more on the actual compression force and less on the distance d. By way of example only, in some versions trocar actuation shaft (32) is longitudinally compliant (e.g., plastically deformable along its length). The compliance of trocar actuation shaft (32) may be selected to enable the compression force being exerted on the tissue by distal face (72) and clamp pad (64) to reach an approximate predetermined value before trocar actuation shaft (32) begins to stretch. Once the compression force reaches the approximate predetermined value, trocar actuation shaft (32) may start stretching, such that further actuation of trocar actuation shaft (32) by knob (26) will not significantly increase the compression force. In some such versions, indicator window (38) may provide a visual indication of the degree to which trocar actuation shaft (32) has stretched, which may be indicative of the compression force being exerted on the tissue by distal face (72) and clamp pad (64). As yet another merely illustrative example, a resilient member (e.g., coil spring, spring stack, etc.) may be interposed between trocar actuation shaft (32) and knob (26). Such a resilient member may similarly provide some degree of stretching once the compression force reaches an approximate predetermined value. Other suitable ways in which instrument (10) may provide compliance of one or more components in response to achievement of an approximate predetermined compression force will be apparent to those of ordinary skill in the art in view of the teachings herein.

II. Exemplary Operation of Ultrasonic Anastomosis Instrument

Figure 6A:
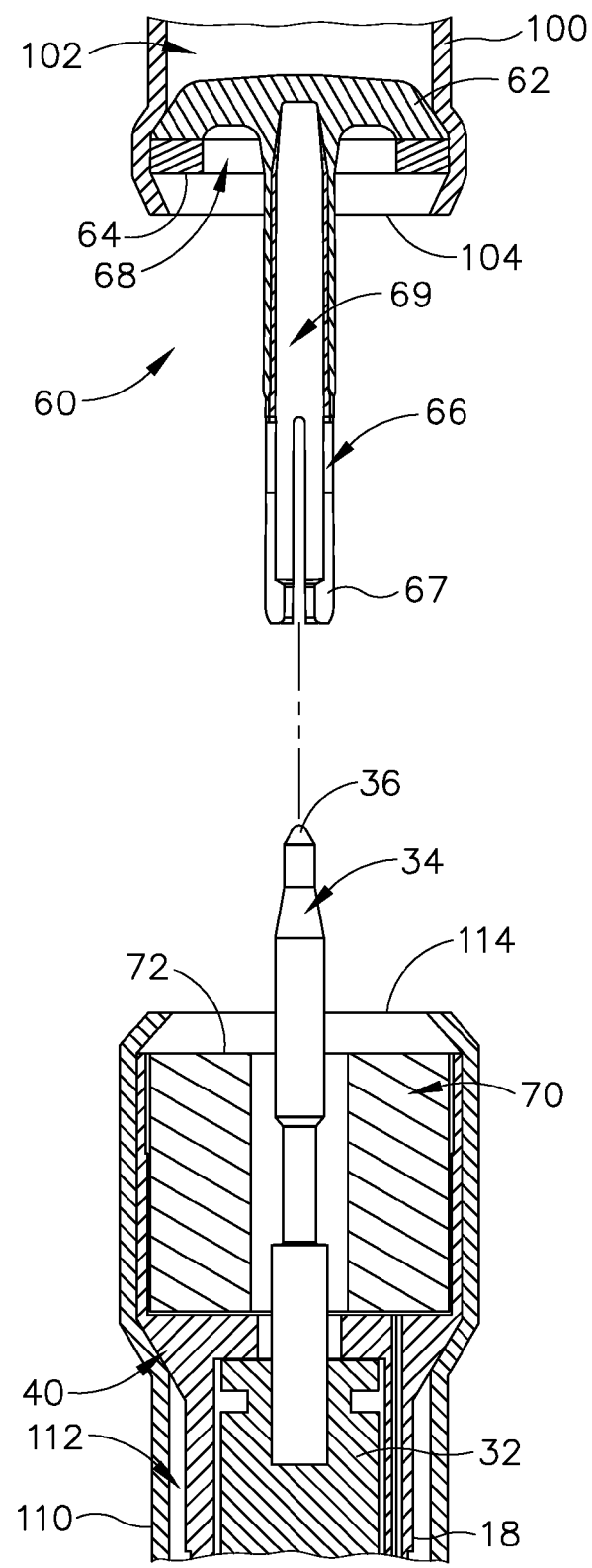
FIG. 6A depicts a side cross-sectional view of the ultrasonic head assembly of FIG. 5 positioned in a first tubular tissue structure, with the anvil separated from the ultrasonic head assembly and positioned in a second tubular tissue structure.
Figure 6B:
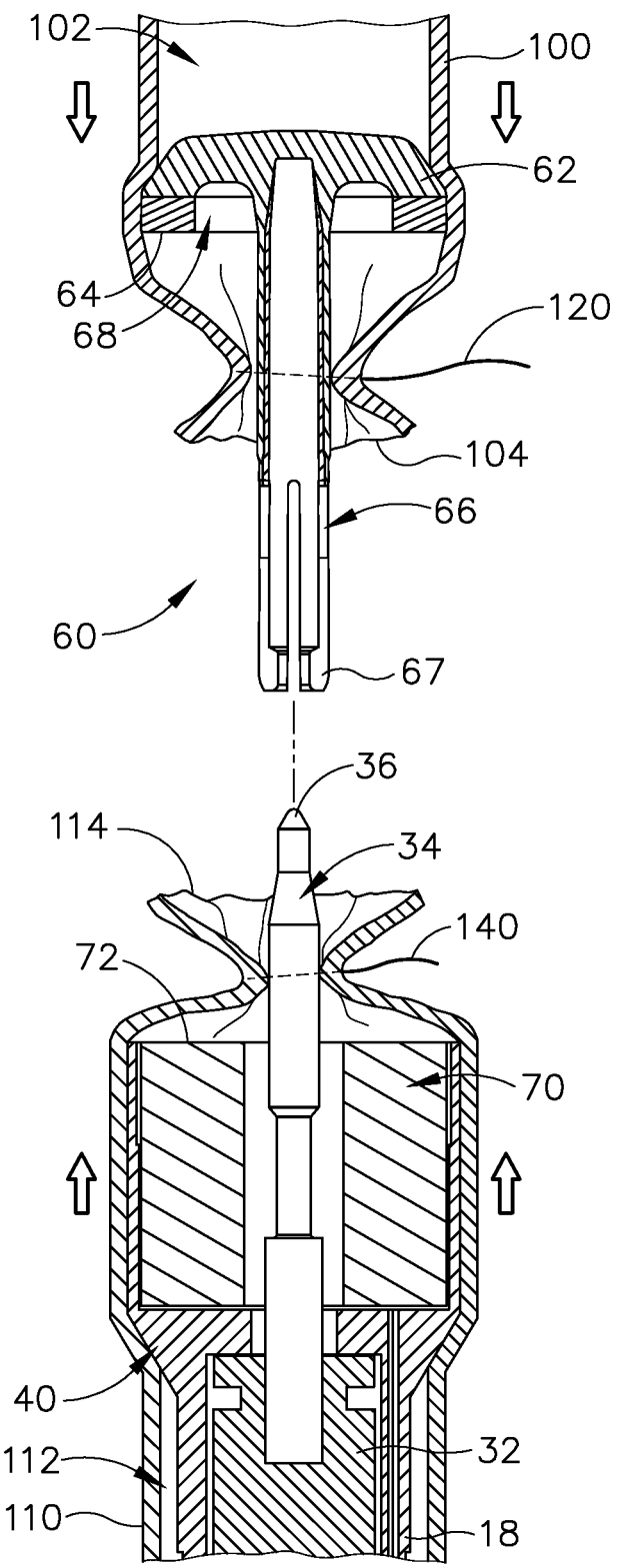
FIG. 6B depicts a side cross-sectional view of the ultrasonic head assembly of FIG. 5, with the first tubular tissue structure sutured about a trocar of the ultrasonic head assembly, with the anvil separated from the ultrasonic head assembly, and with the second tubular tissue structure sutured about a shank of the anvil.
Figure 6C:
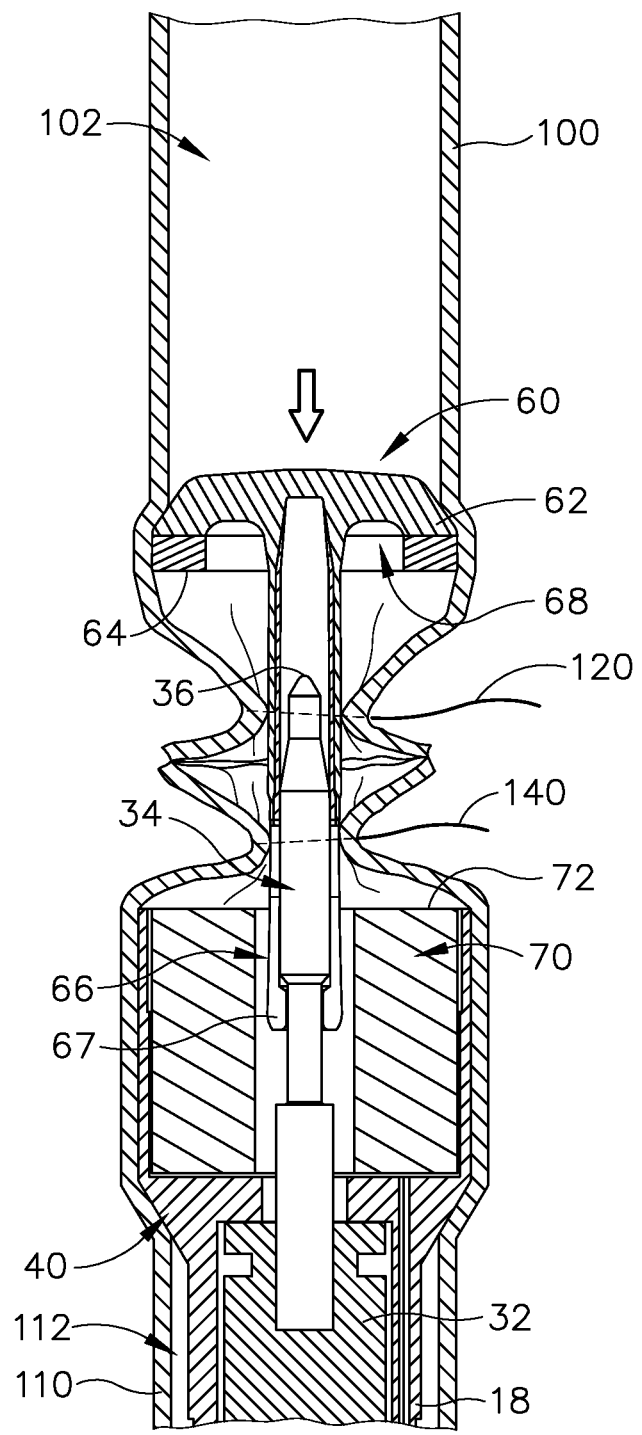
FIG. 6C depicts a side cross-sectional view of the ultrasonic head assembly of FIG. 5, with the shank of the anvil coupled with the trocar of the ultrasonic head assembly.
Figure 6D:
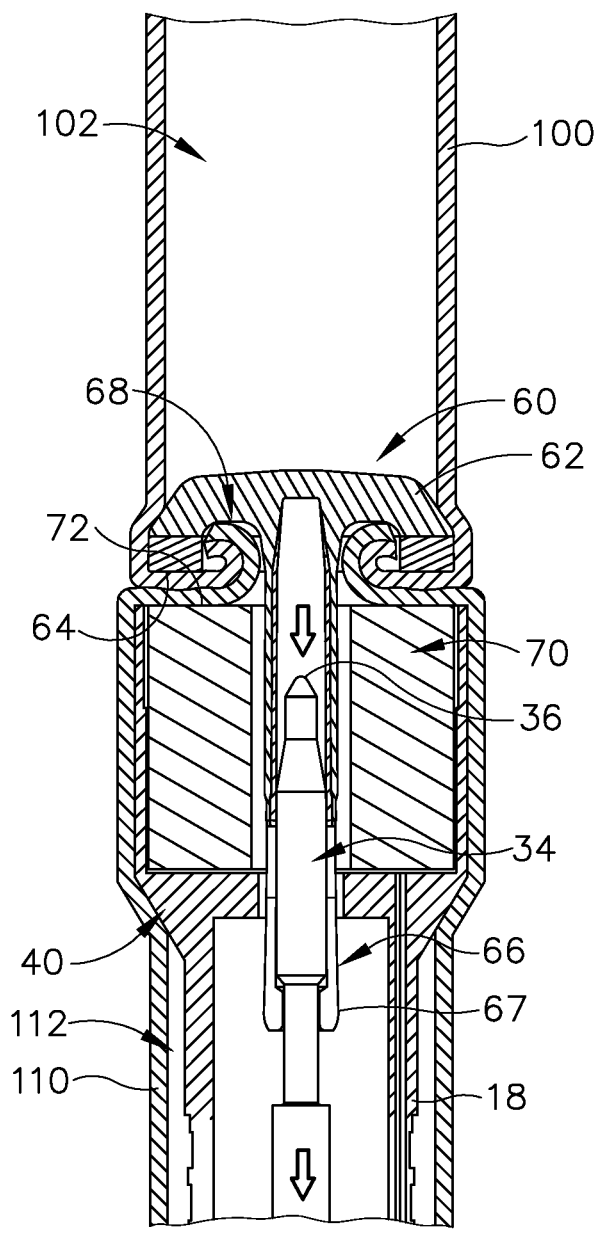
FIG. 6D depicts a side cross-sectional view of the ultrasonic head assembly of FIG. 5, with the shank of the anvil and the trocar of the ultrasonic head assembly retracted into the ultrasonic head assembly to compress regions of the first and second tubular structures between the ultrasonic head assembly and the anvil.
Figure 6E:
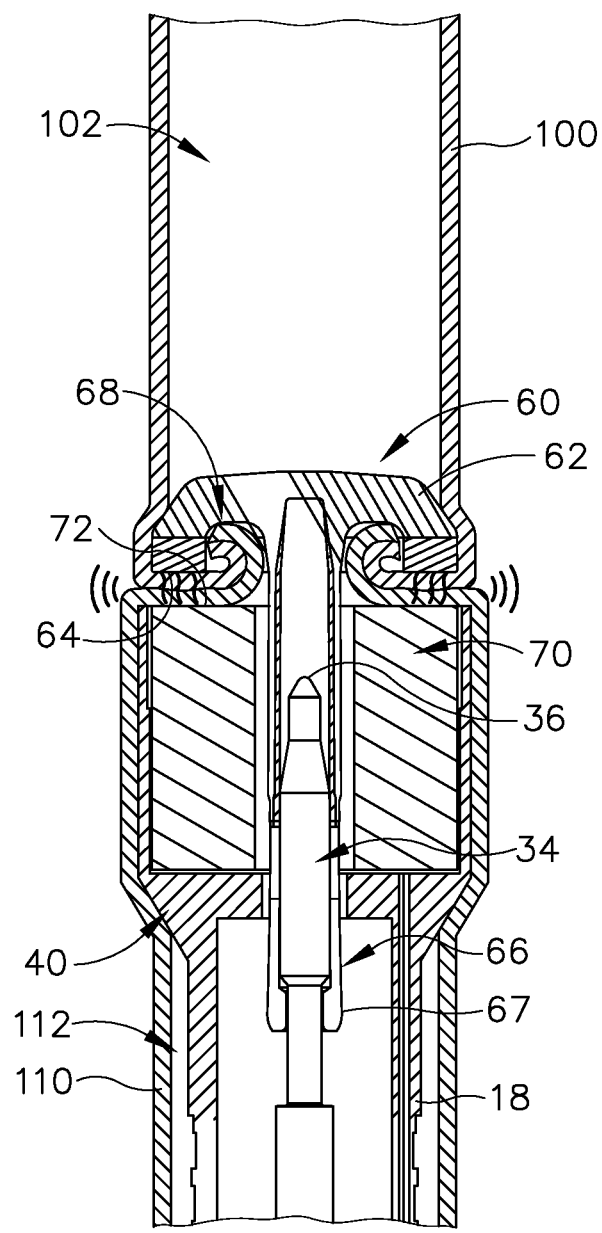
FIG. 6E depicts a side cross-sectional view of the ultrasonic head assembly of FIG. 5, with the transducer element of the ultrasonic head assembly being activated to simultaneously transect and seal the compressed tissue.

FIGS. 6A-6F show a process where instrument (10) is used to join one tubular tissue structure (100) with another tubular tissue structure (110). By way of example only, tissue structures (100, 110) may comprise portions of a patient's intestinal tract (e.g., within the colon, etc.), where the tract has been severed to remove a section of the tract, leaving open free ends (104, 114). As shown in FIG. 6A, ultrasonic head assembly (40) has been inserted through a lower tubular tissue structure (110) such that trocar (34) protrudes from the open free end (114) of the tubular tissue structure (110). Anvil (60) has been inserted through an upper tubular tissue structure (100) such that shank (66) protrudes from the open free end (104) of the tubular tissue structure (100). Various suitable ways in which ultrasonic head assembly (40) and anvil (60) may be placed in the positions shown in FIG. 6A will be apparent to those of ordinary skill in the art in view of the teachings herein.

After ultrasonic head assembly (40) and anvil (60) have been placed in the positions shown in FIG. 6A, the open free end (104) of the upper tubular tissue structure (100) is pulled over a portion of shank (66) of anvil (60), as shown in FIG. 6B. Similarly, the open free end (114) of the lower tubular tissue structure (110) is pulled over a portion of trocar (34), as also shown in FIG. 6B. A suture (120) is then passed through the upper tubular tissue structure (100) in a purse-string configuration, with the suture (120) being drawn to generally tighten the upper tubular tissue structure (100) against shank (66). A suture (140) is also passed through the lower tubular tissue structure (110) in a purse-string configuration, with the suture (140) being drawn to generally tighten the lower tubular tissue structure (110) against shank (66). It should be understood that this technique is merely optional. Various other suitable ways in which upper tubular tissue structure (100) may be secured to anvil (60), as well as various other suitable ways in which lower tubular tissue structure (110) may be secured to ultrasonic head assembly (40), will be apparent to those of ordinary skill in the art in view of the teachings herein.

Once tubular tissue structures (100, 110) have been secured to anvil (60) and ultrasonic head assembly (40), respectively, trocar (34) is inserted into bore (69) of shank (66) until leaves (67) snap onto trocar (34) as shown in FIG. 6C. By way of example only, this may be accomplished by grasping an exposed portion of shank (66) with a set of conventional tissue graspers and then pulling shank (66) toward trocar (34). Other suitable techniques and instruments that may be used to secure shank (66) and trocar (34) together as shown in FIG. 6C will be apparent to those of ordinary skill in the art in view of the teachings herein. It should also be understood that the movement of anvil (60) toward ultrasonic head assembly (40) will pull tubular tissue structure (100) toward tubular tissue structure (110).

With shank (66) and trocar (34) secured together, the operator may then rotate knob (26) to retract anvil (60) proximally relative to ultrasonic head assembly (40), thereby reducing the gap distance d between clamp pad (64) and distal face (72) of transducer element (70) as shown in FIG. 6D. As described above, this rotation of knob (26) is converted into retraction of trocar (34) via trocar actuation assembly (30) and trocar actuation shaft (32). The operator may monitor the gap distance d by viewing indicator window (38). It should be understood that the tissue captured between clamp pad (64) and distal face (72) of transducer element (70) may be in a substantially compressed state when the desired gap distance d has been achieved. As noted above, a complaint feature of trocar actuation shaft (32) (and/or a compliant feature coupled with trocar actuation shaft (32)) may begin to plastically deform once a suitable compression force has been achieved between clamp pad (64) and distal face (72) of transducer element (70). Transducer element (70) may also experience longitudinally directed compressive force at this stage. It should also be understood that tissue located interior to the inner diameter of clamp pad (64) may gather within recess (68) at this stage.

Figure 6F:
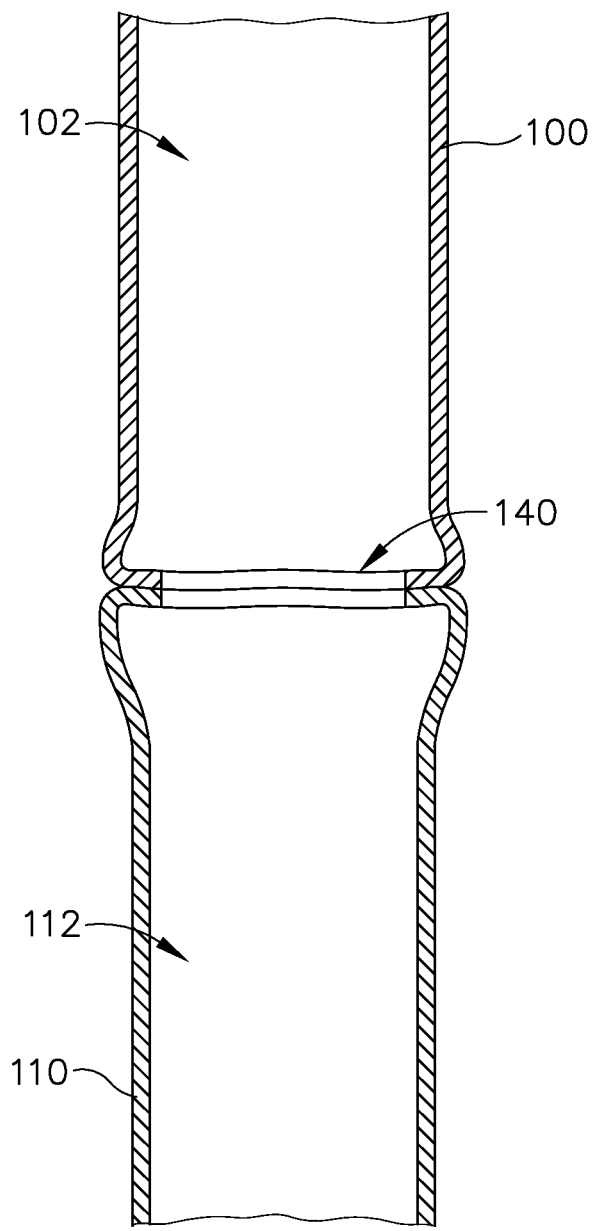
FIG. 6F depicts a side cross-sectional view of the first and second tubular structures joined together at an anastomosis site.

Once the desired gap distance d and/or compression force has been achieved, the operator may actuate trigger assembly (24), thereby activating transducer element (70) with ultrasonic energy as shown in FIG. 6E. The ultrasonic vibrations generated by transducer element (70) will transect and seal the tissue captured between clamp pad (64) and distal face (72). In particular, the tissue gathered within recess (68) will be transected from the rest of tubular tissue structures (100, 110); and the adjacent apposed tissue regions of tubular tissue structures (100, 110) will be sealed together, resulting in a generally annular configuration of sealed layers of tissue. The operator may then remove instrument (10) from the patient (e.g., via lumen (112) of tubular tissue structure (110)), leaving behind a sealed anastomosis (140) as shown in FIG. 6F. The transected tissue in recess (68) may be removed with instrument (10). It should be understood that the resulting anastomosis (140) may provide a clear path for fluid communication between the lumen (102) of first tubular tissue structure (100) and the lumen (112) of second tubular tissue structure (110). It should also be understood that the anastomosis (140) may have sufficient structural integrity to withstand forces that would be communicated on/along/through tubular tissue structures (100, 110) during normal biological processes, such that contents passing through lumens (102, 112) and anastomosis (140) will not leak at the site of anastomosis (140).

It should be understood that anvil (60) may remain coupled with trocar (34) when instrument (10) is removed from the patient as shown in the transition from FIG. 6E to FIG. 6F. In some instances, after completing the stage shown in FIG. 6E and before removing instrument (10) as shown in FIG. 6F, the operator may rotate knob (26) in an opposite direction to increase the gap distance d between clamp pad (64) and distal face (72) of transducer element (70). This may assist in the release of tissue at the anastomosis, which may facilitate removal of instrument (10) without damaging the anastomosis (140).

In some instances, transducer assembly (70) may be activated repeatedly at the same anastomosis (140) site, without having to remove ultrasonic head assembly (40) from the patient between activations. Furthermore, transducer assembly (70) may be activated at various sites within a patient, without having to remove ultrasonic head assembly (40) from the patient between activations. It should therefore be understood that instrument (10) may better lend itself to repeated firings than a conventional circular stapler instrument. Moreover, instrument (10) of the present example does not leave man-made components like staples within the patient after anastomosis (140) is complete.

While the example depicted in FIGS. 6A-6F and described above relates to an end-to-end anastomosis, it should be understood that instrument (10) may also be readily used to perform a side-to-side anastomosis. Other suitable ways in which instrument (10) may be used will be apparent to those of ordinary skill in the art in view of the teachings herein.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a shaft extending distally from the body, wherein the shaft has a distal end, wherein the distal end of the shaft includes a shroud, wherein the shroud comprises a distally presented face;
   (c) an ultrasonic transducer disposed within the shroud, wherein the ultrasonic transducer includes a distally presented annular face and a proximally presented annular face, wherein the proximally presented annular face of the ultrasonic transducer abuts against the distally presented face of the shroud, wherein the ultrasonic transducer defines a central bore; and
   (d) an annular clamp pad, wherein the clamp pad is movable toward the distally presented annular face of the ultrasonic transducer.

2. The apparatus of claim 1, wherein the body comprises a handle assembly.

3. The apparatus of claim 1, wherein the shaft is curved.

4. The apparatus of claim 1, wherein the ultrasonic transducer has a cylindraceous configuration.

5. The apparatus of claim 1, further comprising one or more electrical conductors extending through the shaft from the body to the ultrasonic transducer.

6. The apparatus of claim 1, wherein the central bore extends through the distally presented face.

7. The apparatus of claim 6, further comprising an elongate member extending through the central bore of the ultrasonic transducer, wherein the elongate member is operable to selectively move the clamp pad toward and away from the distally presented annular face of the ultrasonic transducer.

8. The apparatus of claim 7, wherein the elongate member comprises a trocar.

9. The apparatus of claim 7, further comprising an anvil, wherein the anvil comprises:
   (i) a head, wherein the clamp pad is secured to the head, and
   (ii) a shank extending from the head, wherein the shank is configured to couple with the elongate member.

10. The apparatus of claim 9, wherein the head defines a recess interior to the clamp pad.

11. The apparatus of claim 1, wherein the shroud is configured to exert inwardly directed compression on an outer region of the ultrasonic transducer.

12. The apparatus of claim 1, wherein the shroud includes a distal edge, wherein the distally presented annular face is flush with the distal edge.

13. The apparatus of claim 1 wherein the ultrasonic transducer is configured to vibrate ultrasonically in a longitudinal motion and in a radial motion.

14. The apparatus of claim 1, wherein the clamp pad includes a substance configured to enhance hemostasis or healing of tissue.

15. The apparatus of claim 1, further comprising a generator operable to provide electrical power to the ultrasonic transducer, wherein the generator is coupled with the body via a cable.

16. An apparatus comprising:
   (a) a body;
   (b) a shaft extending distally from the body, wherein the shaft has a hollow distal end defining an interior surface;
   (c) a cylindraceous ultrasonic transducer located at the distal end of the shaft, wherein the cylindraceous ultrasonic transducer comprises:
      (i) an exterior surface in contact with the interior surface of the hollow distal end along at least a nodal point of the cylindraceous ultrasonic transducer, and
      (ii) a distally presented flat annular face;
   (d) an anvil coupling feature, wherein the anvil coupling feature is translatable relative to the cylindraceous ultrasonic transducer; and
   (e) an anvil, wherein the anvil is configured to couple with the anvil coupling feature, wherein the anvil comprises an annular clamp pad, wherein the clamp pad is movable toward the distally presented flat annular face of the cylindraceous ultrasonic transducer to capture tissue of two anatomical structures between the clamp pad and the distally presented flat annular face of the cylindraceous ultrasonic transducer;
   wherein the cylindraceous ultrasonic transducer is configured to transect and secure an anastomosis between the two anatomical structures captured between the distally presented flat annular face of the cylindraceous ultrasonic transducer and the annular clamp pad of the anvil.

17. An apparatus comprising:
   (a) a body;
   (b) a shaft extending distally from the body, wherein the shaft has a distal end;
   (c) an ultrasonic element located at the distal end of the shaft, wherein the ultrasonic element includes a distally presented annular face, a proximally presented annular face, an exterior surface, and an interior surface, wherein the interior surface defines a bore extending from the distally presented annular face to the proximally presented annular face, wherein the interior surface and the exterior surface are electrically conductive, wherein the proximally presented annular face and the distally presented annular face are both electrically insulated, wherein the exterior surface is in contact with the distal end of the shaft;
   (d) an annular clamp pad, wherein the clamp pad is movable toward the distally presented annular face of the ultrasonic element; and
   (e) an activation element positioned on the body and in electrical communication with either the exterior surface or the interior surface of the ultrasonic element, wherein the ultrasonic element is configured to be activated in response to actuation of the activation element.

\* \* \* \* \*